United States Patent [19]
Bernstein

[11] Patent Number: 6,004,322
[45] Date of Patent: Dec. 21, 1999

[54] MODULAR PEDICLE SCREW SYSTEM

[75] Inventor: Avi J. Bernstein, Wilmette, Ill.

[73] Assignee: SDGI Holdings, Inc., Wilmington, Del.

[21] Appl. No.: 08/707,025

[22] Filed: Sep. 10, 1996

Related U.S. Application Data

[63] Continuation of application No. 08/328,833, Oct. 25, 1994, abandoned.

[51] Int. Cl.$^6$ .................................................. A61B 17/70
[52] U.S. Cl. ............................................ 606/61; 606/73
[58] Field of Search ................................ 606/61, 60, 72, 606/73, 59; 623/17

[56] References Cited

U.S. PATENT DOCUMENTS

| | | |
|---|---|---|
| 2,439,995 | 4/1948 | Thrailkill . |
| 2,627,855 | 2/1953 | Price . |
| 4,569,338 | 2/1986 | Edwards . |
| 4,648,388 | 3/1987 | Steffee ...................................... 606/59 |
| 4,854,311 | 8/1989 | Steffee . |
| 4,887,585 | 12/1989 | Nutt . |
| 4,946,458 | 8/1990 | Harms et al. . |
| 4,987,892 | 1/1991 | Krag et al. . |
| 5,024,213 | 6/1991 | Asher et al. . |
| 5,047,029 | 9/1991 | Aebi et al. . |
| 5,053,034 | 10/1991 | Olerud . |
| 5,084,049 | 1/1992 | Asher et al. . |
| 5,113,685 | 5/1992 | Asher et al. . |
| 5,129,899 | 7/1992 | Small et al. . |
| 5,129,900 | 7/1992 | Asher et al. . |
| 5,196,014 | 3/1993 | Lin . |
| 5,217,461 | 6/1993 | Asher et al. . |
| 5,242,443 | 9/1993 | Kambin ...................................... 606/61 |
| 5,257,994 | 11/1993 | Lin . |
| 5,261,909 | 11/1993 | Sutterlin et al. . |
| 5,275,601 | 1/1994 | Gogolewski et al. ..................... 606/72 |
| 5,344,422 | 9/1994 | Frigg .......................................... 606/61 |
| 5,470,333 | 11/1995 | Ray ........................................... 606/61 |
| 5,474,551 | 12/1995 | Finn et al. ................................. 606/61 |
| 5,480,440 | 1/1996 | Kambin ..................................... 606/60 |
| 5,487,744 | 1/1996 | Howland .................................... 606/61 |
| 5,501,684 | 3/1996 | Schlapfer et al. ......................... 606/73 |
| 5,520,688 | 5/1996 | Lin ............................................ 606/61 |
| 5,609,592 | 3/1997 | Brumfield et al. ........................ 606/61 |

FOREIGN PATENT DOCUMENTS

| | | |
|---|---|---|
| 468264 | 1/1992 | European Pat. Off. ................. 606/61 |
| 553424 | 8/1993 | European Pat. Off. ................. 606/61 |
| 611116 | 8/1994 | European Pat. Off. ................. 606/61 |
| 1136123 | 12/1956 | France . |
| 0086969 | 4/1966 | France . |
| 2671966 | 7/1992 | France . |
| 2090745 | 7/1982 | United Kingdom . |

OTHER PUBLICATIONS

Smith & Nephew Spine's Kambin Offset Bolt Advertisement.

*Primary Examiner*—Michael Buiz
*Assistant Examiner*—David O. Reip
*Attorney, Agent, or Firm*—Woodard, Emhardt, Naughton, Moriarty & McNett

[57] ABSTRACT

A modular pedicle screw system for use with a longitudinal member, such as a plate or rod, having a fastener with a threaded lower portion for engaging a spinal element and an upper portion adapted to receive a headpiece. The headpiece is adapted to mate with the upper portion of the fastener and to engage a longitudinal member. A plurality of headpieces having angulated projections, lateral sections, and angulated lateral sections, all of which are adapted to engage a longitudinal member and overcome angular and translational malalignment of the fastener, may also be provided.

49 Claims, 4 Drawing Sheets

MODULAR PEDICLE SCREW SYSTEM

This application is a continuation of application Ser. No. 08/328,833 filed on Oct. 25, 1994, now abandoned.

BACKGROUND OF THE INVENTION

The present invention relates to a method and apparatus which is used to retain spinal elements in a spatial relationship. More particularly, a modular pedicle screw assembly of the invention consists of a base fastener and connecting headpieces which are varied in length and angularity in order to provide a clinician a greater degree of flexibility in stabilizing the spine when performing spinal fusions in the cervical, thoracic, and lumbar regions.

Important considerations for spinal instrumentation used to promote spinal fusion are safe insertion, rigid fixation, and ease and adaptability of implantation. Historically, Harrington rods were an early type of spinal instrumentation used to stabilize the thoracic and the upper lumbar regions to obtain correction and stability for fusion. This instrumentation involved long rods attached to hooks, which were inserted over the bony arches (lamina) of the spinal canal. The instrumentation was subject to failure when the hooks either broke the lamina or became displaced and thus, the intended stabilization and correction was lost.

Subsequent spinal instrumentation included the use of a longitudinal member, such as a plate, to interconnect a series of pedicle screws such as that disclosed in U.S. Pat. No. 5,129,899 issued to Laura C. Small ("Small, et al"). In this system, the clinician must strive to place the series of pedicle screws into the bone in longitudinal alignment with as little lateral displacement and angular deflection as possible so that the plate may be attached to the series of pedicle screws in order to achieve a solid biomechanical relationship. However, due to variances in the spinal column or imperfect placement by the clinician, the screws are often inserted at an angle or must be placed laterally outside the longitudinal axis defined by the plate and other screws. While slight angular deviations of screw placement of up to 20° may be overcome by the use of contoured washers, larger angular deflections and the problems associated with lateral displacement of the pedicle screws cannot be overcome by the instrumentation disclosed in the Small, et al. patent.

The development of the Kambin Offset Bolt for the use with the device disclosed in the Small, et al. patent allows greater flexibility when the pedicle screws cannot be placed in the desired longitudinal relationship. The Kambin system, which is offered by Smith & Nephew and known to those of skill in the art, uses bolts having lateral extensions that allow attached threaded shanks to reach the plates in a more desirable biomechanical relationship. The offset bolt, however, has several drawbacks. First, insertion of the offset bolt requires a larger area of clearance to obtain insertion. This often leads to insertion difficulty when the bolt interferes with the spinal retractors, other elements of the spine, or other screws which have already been implanted. This interference can cause other implanted screws to loosen when impinged. In addition, once in place, the offset bolt can only overcome translational malalignment, but not angular malalignment of the pedicle screws.

Another system is disclosed in U.S. Pat. No. 5,129,900 ("Asher, et al."). There, pedicle screws are connected to a longitudinal member, such as a rod. Lateral deviations may be cured by the use of connector members which include oblong openings. (Col. 4 lines 54–67). Like the offset screw taught by the Small et al. patent, however, the device disclosed in the Asher, et al. patent cannot overcome the difficulties associated with angular malalignment.

SUMMARY OF THE INVENTION

The present invention preserves the advantages of using a pedicle screw and longitudinal member while providing new features and advantages not found in the previous instrumentation. Specifically, the invention overcomes both translational malalignment and angular malalignment by providing a modular pedicle screw system having a fastener adapted to receive a plurality of headpieces with various angular and lateral length configurations which are, in turn, connected to a longitudinal member or members to obtain rigid stabilization of the spine.

In one embodiment of the present invention, a pedicle screw is provided having an exterior thread along its lower portion and an upper portion adapted to securely receive a headpiece. The headpiece includes a neck which has a bore that defines an inner wall having a mating surface which is adapted to slidingly engage or mate with a mating surface defined by the outer wall of the upper portion of the headpiece. The headpiece further includes a projection which terminates in a connector which is adapted to engage a longitudinal member such as a plate or rod.

In another embodiment of the present invention, the mating surface of the outer wall of the upper portion of the pedicle screw is frusto-conical in shape with a fluted outer or "male" surface; the headpiece including a corresponding inner or "female" portion. Mating the two components in this manner provides greater lateral and rotational stability as well as greater ease of insertion.

In yet another embodiment of the present invention, an angulated headpiece is provided. The headpiece of this embodiment includes a neck portion having a projection which extends out of the neck at various angulations and terminates with a connector for engaging a longitudinal member. Angulating the projection allows for the correction of angular malalignment of the fastener.

In still another embodiment of the present invention, a translational headpiece is provided. The headpiece of this embodiment includes lateral sections which extend outwardly from the neck and may range in length from about 5 millimeters to 3 centimeters. The lateral sections also terminate in a connector for engaging a longitudinal member and allow for the correction of translational malalignment of the fastener.

In a further embodiment of the present invention, an angulated translational headpiece is provided. The headpiece of this embodiment includes angulated lateral sections which extend outwardly from the headpiece's neck at various angles and lengths. These sections also terminate in a connector for engaging a longitudinal member and allow for the correction of both angular and translational malalignment of the fastener.

Not only does the present invention provide the clinician with the flexibility and adaptability needed to overcome difficult malalignment problems, it offers the patient a number of safety benefits as well. First, the present invention reduces the stress placed on both the placed fastener and patient's bone by reducing the need to manipulate malaligned fasteners. Second, the integrity of the patient's bone is maintained by eliminating the number of placements into the bone since malaligned fasteners do not need to be removed and/or relocated when the present invention is used by the clinician.

Accordingly, an object of the present invention is to provide a modular pedicle screw system and method of implanting the same which is more flexible, safer and easier to implant than present spinal instrumentation and methods.

Another object of the present invention is to provide a modular pedicle screw system and method which can overcome translational malalignment of the fastener.

A further object of the present invention is to provide a modular pedicle screw system and method which can overcome angular malalignment of the fastener.

Yet another object of the present invention is to provide a modular pedicle screw system and method which can overcome both translational and angular malalignment of the fastener.

Still another object of the present invention is to provide a modular pedicle screw system and method which uses a fastener and headpiece having corresponding mating shapes in order to improve both the lateral and rotational stability between the two pieces.

Yet a further object of the present invention is to provide a modular pedicle screw system and method that can be used in combination with existing pedicle screw system employing either longitudinal plates or rods.

BRIEF DESCRIPTION OF THE DRAWINGS

These and other features, objects and advantages of the present invention will become apparent from the following description and drawings wherein like reference numerals represent like elements in the several views, and in which.

DETAILED DESCRIPTION OF THE PREFERRED EMBODIMENTS

Figure 1:
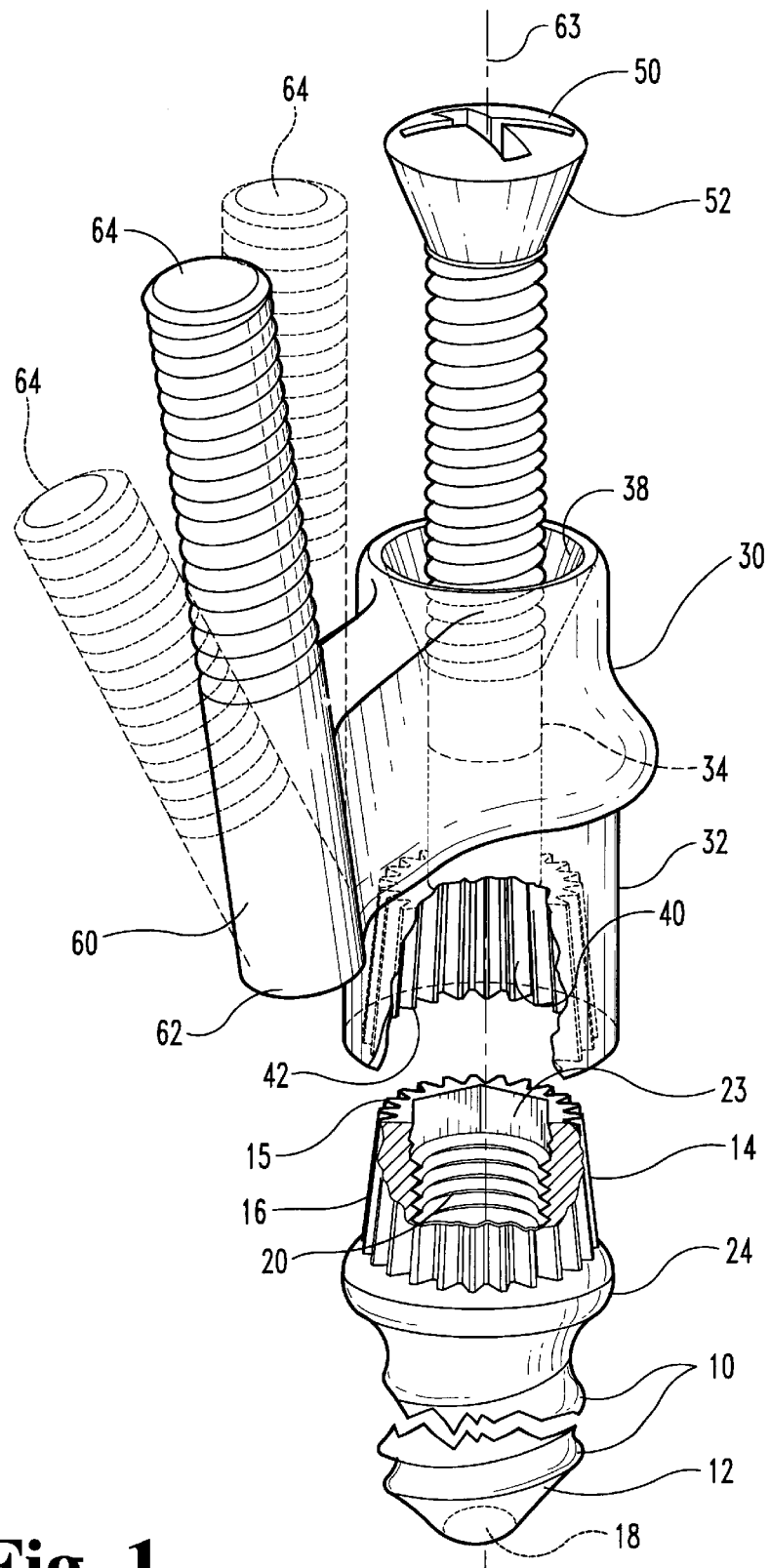
FIG. 1 is a perspective view of an embodiment using an angulated headpiece having a connector adapted to engage a plate-like longitudinal member and with portions removed to reveal aspects of the invention.

In accordance with a preferred embodiment as shown in FIG. 1, the modular pedicle screw system includes a pedicle screw or fastener 10; a headpiece 30 which is adapted to engage fastener 10; and, a locking element 50 which mechanically affixes fastener 10 to headpiece 30.

Figure 2:
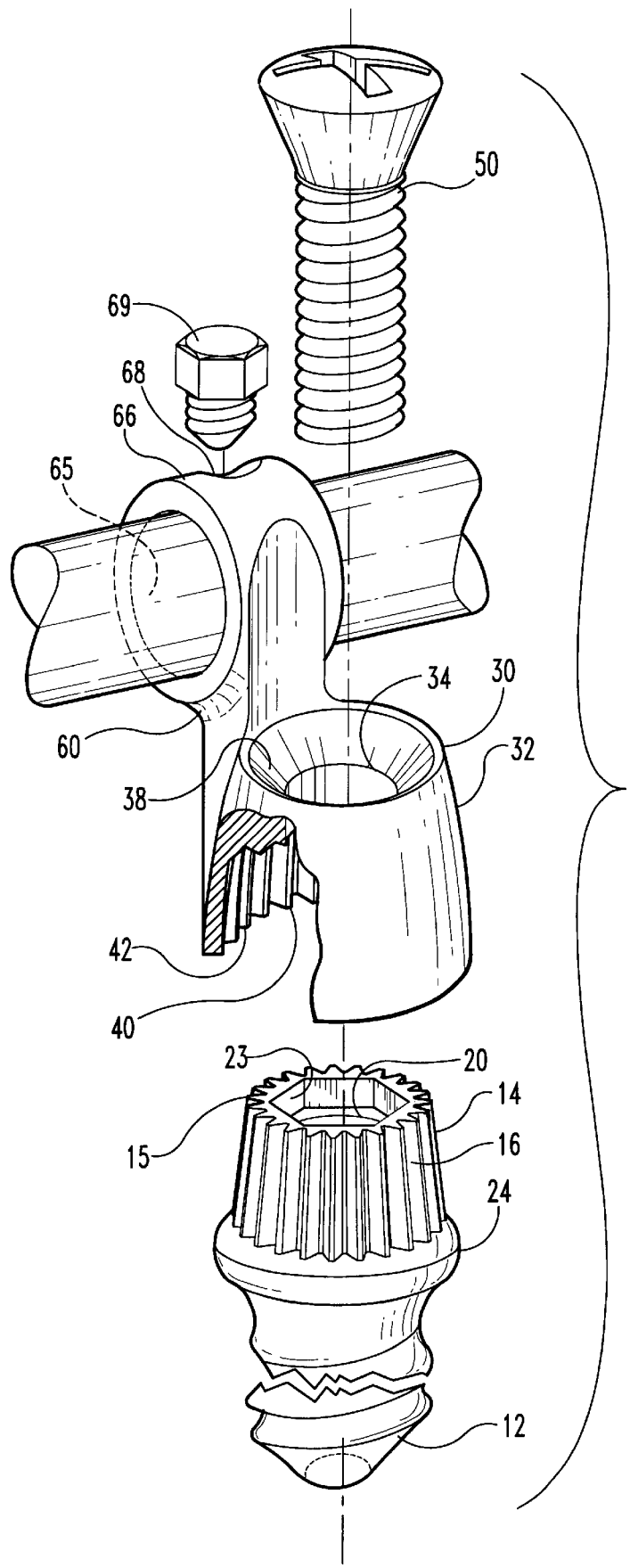
FIG. 2 is a perspective view of the embodiment shown in FIG. 1 which is designed to work with a rod-like longitudinal member and has portions removed to reveal aspects of the invention.

Fastener 10 also includes a threaded lower portion 12 for engaging a spinal element and an upper portion 14 which defines an outer wall having a mating surface that is adapted to allow for the sliding engagement of fastener 10 to headpiece 30. One suitable configuration for upper portion 14 that provides rotational and lateral stability is a frusto-conical shape 15 having fluted edges 16 on its outer surface as shown in FIGS. 1 and 2. Upper portion 14 may also be configured as a cylinder, square, hex, or in other shapes persons of ordinary skill would recognize.

Fastener 10 further includes a bore 18 which allows fastener 10 to be cannulated during insertion. The diameter of bore 18 is increased near upper portion 14 to form an internal threaded portion 20 for receiving locking element 50. Bore 18 of fastener 14 may also terminate in a hexed-shaped recess 23 which provides a surface that can engage a suitable insertion tool (not shown). A shoulder 24 may also be provided which acts as a stop that limits the depth fastener 10 can be inserted.

As shown in FIGS. 1 and 2, headpiece 30 includes a neck portion 32 having cylindrical aperture 34 with engagement surface 38. Engagement surface 38 is dimensioned so as to allow head 52 of locking element 50 to form a secure fit with upper surface 38 when inserted.

Neck 32 further includes a bore or recess 40 which defines an inner wall having a mating surface that is adapted to slidingly engage or mate with upper portion 14 of fastener 10. In the embodiment using a frusto-conical shape, the inner wall would have a similarly configured mating surface 42 and would be configured to mate with the frusto-conical shape of outer wall 15. The inner wall may also have other configurations designed to mate with the other shapes described above. By mating upper portion 14 of fastener 10 with recess 40 of headpiece 30 both lateral and rotational stability between the two pieces may be achieved.

There are a number of variations of headpiece 30 which are built upon the basic structure of headpiece 30 as described above. One is an angulated headpiece 60 (also shown as headpiece 30 of FIGS. 1 and 2), which includes a projection 62 that extends out of neck 32 as shown in FIG. 1. Projection 62 terminates in a connector which can be either a threaded shank 64 (as shown in FIG. 1) or a rod connector 66 having an engagement aperture 65, a threaded bore 68 and a locking screw 69 (as shown in FIG. 2), which are, in turn, adapted to secure a longitudinal member such as plate of a design similar to that disclosed in the Small, et al. patent or a rod 65 of a design similar to that disclosed in the Asher, et al. patent, respectively.

Other headpiece variations, which will be described below, may also terminate in these connectors, but persons of ordinary skill in the art would also recognize that the headpieces may be adapted to work with other types of longitudinal support members as well. Since one of the purposes of the invention is to overcome angular malalignment, projection 62 of angulated headpiece 60 is angled with respect to centerline 63 of headpiece 60 as shown in FIG. 1. The degrees of angulation of projection 62 should vary but should include angulations in the range of about 5° to 45°.

Figure 3:
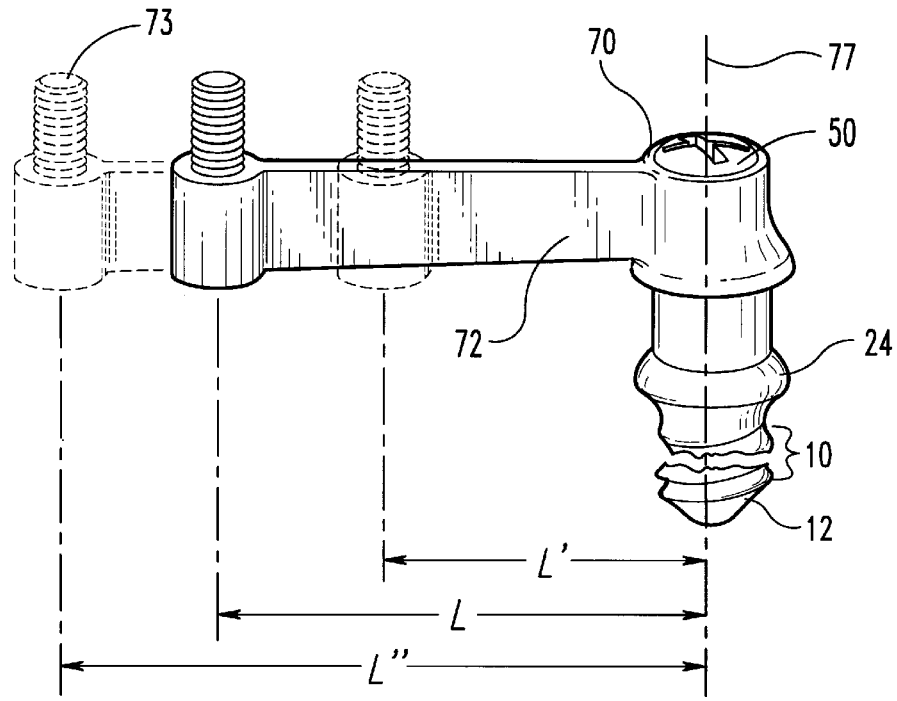
FIG. 3 is a perspective view of an embodiment having a translational headpiece consisting of a plurality of lateral length sections.

FIG. 3 illustrates translational headpiece 70. Translational headpiece 70 includes lateral section 72 which extends outwardly from centerline 77 of headpiece 70 and terminates with a connector 73 as described above. To provide the greatest degree of flexibility to a clinician, the length (L,L', L") of section 72 should vary and include typical lengths ranging from about 5 millimeters to 3 centimeters.

Figure 4:
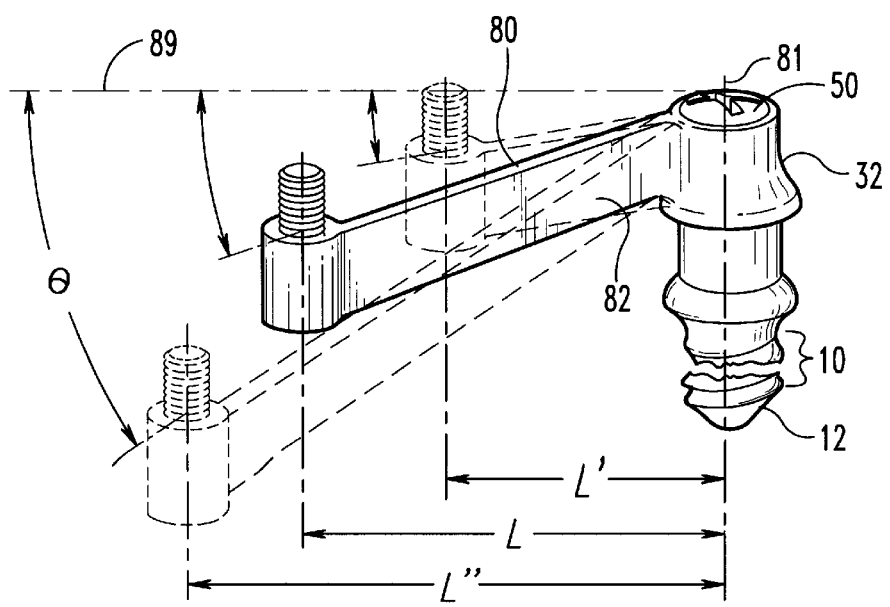
FIG. 4 is a perspective view of an embodiment having an angulated translational headpiece consisting of a plurality of angular and lateral length configurations.

As shown in FIG. 4, another headpiece embodiment is an angulated translational headpiece 80, which is a combination of the previously described headpiece embodiments. Headpiece 80 includes lateral section 82 which extends outwardly from centerline 81 of headpiece 80. In addition, section 82 is also angulated with respect to a horizontal axis shown as line 89. The degrees of angulation (θ) should vary and may include angulations in the range of about 2° to 45°. The lengths (L,L',L") of section 82 should also vary as described above.

Figure 5:
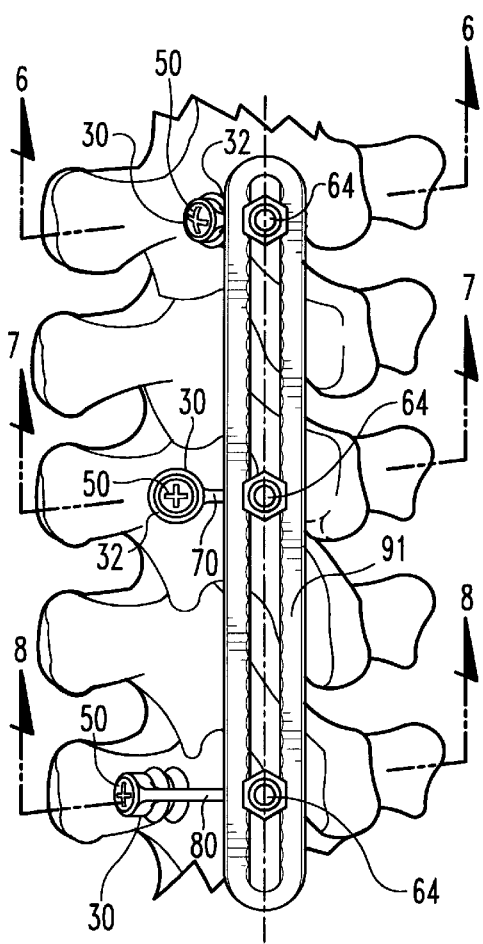
FIG. 5 is a posterior view of a spinal section in which an apparatus constructed in accordance with the present invention has been implanted.

By providing a modular pedicle screw system with a fastener that accommodates a plurality of at least three different headpieces with various lateral section lengths, various angulated projections and a combination of the two provides the clinician with a system which can overcome many of the malalignment problems encountered during the implantation of spinal instruments as shown in FIG. 5.

Figure 6:
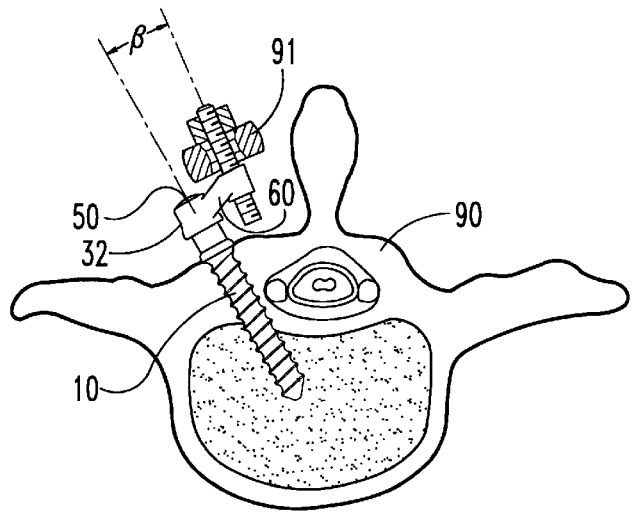
FIG. 6 is an enlarged view, partly in section taken generally along the line 6—6 of FIG. 5, illustrating an embodiment threaded into a spinal element and overcoming angular malalignment of the fastener.

In situations involving primarily angular malalignment as shown in FIGS. 5 and 6, fastener 10 will first be secured to a spinal element 90 by a suitable insertion tool which may be a hex-shaped wrench or a wrench having a bore designed to mate with upper portion 14. The clinician will then select one of the angulated headpieces 60 which best compensates for the angular malalignment, if any, and returns the threaded shank or rod connector to a position where it is once again is in longitudinal alignment with the longitudinal member 91 and other fasteners. The headpiece and fastener will then be secured together by set screw 50, and ultimately, a longitudinal member will be securingly retained by a connector as previously described.

Figure 7:
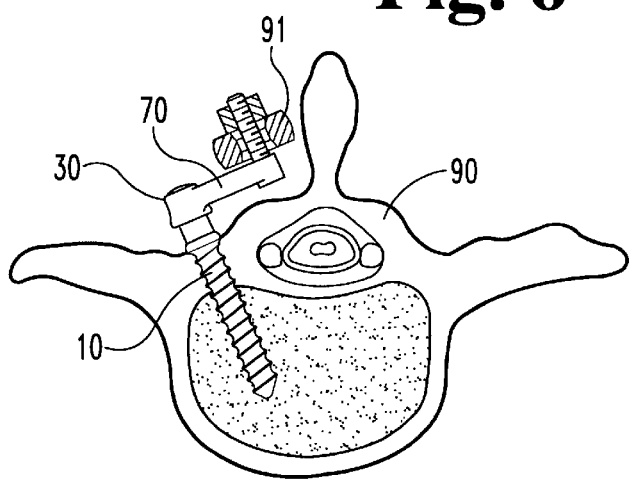
FIG. 7 is an enlarged view, partly in section taken generally along the line 7—7 of FIG. 5, illustrating an embodiment threaded into a spinal element and overcoming lateral malalignment of the fastener.

In situations involving primarily translational malalignment, as shown in FIGS. 5 and 7, fastener 10 will first be secured to a spinal element 90. The clinician will then select one of the translational headpieces 70 which best compensates for the malalignment and returns connector 73 to a position of proper alignment for securing a longitudinal member 91. Moreover, since the headpiece and fastener are slidingly engaged, the device can be implanted in areas in which there is very little clearance in which to manipulate the headpiece. For example, in instances in which a translational headpiece is used, a fastener can first be inserted and then the headpiece is slid onto the upper portion of the fastener before the two piece are affixed together. By eliminating the need to thread the two pieces together, this arrangement can be used in situations where potential interference from spinal retractors, other elements of the spine, or the other screws which have already been implanted may be encountered. Thus, the clinician can use the present invention in areas which may not be accessible to other offset bolts currently available.

Figure 8:
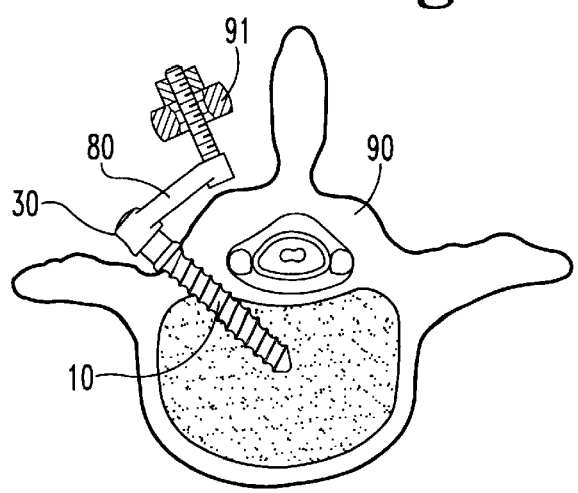
FIG. 8 is an enlarged view, partly in section taken generally along the line 8—8 of FIG. 5, illustrating an embodiment threaded into a spinal element and overcoming both angular and lateral malalignment of the fastener.

In situations presenting both translational and angular malalignment, as shown in FIGS. 5 and 8, an angulated translational headpiece 80 is used. Again, fastener 10 is first inserted into spinal element 90. The clinician then selects the appropriate headpiece with the correct lateral length and angular deflection which will compensate for the malalignment as shown in FIGS. 5 and 8.

While the preferred embodiments of the present invention have been illustrated and described, it will be understood by those of ordinary skill in the art that changes and other modifications can be made without departing from the invention in its broader aspects. Accordingly, persons of ordinary skill in the art would further recognize that the modular pedicle screw system of this invention may also be useful and could be adapted for use with other applications employing different longitudinal members other than rods or plates.

What is claimed is:

1. A modular bone screw system for use with a longitudinal member comprising:
    a fastener having an upper portion defining an outer wall having a first mating surface and a threaded lower portion for securing said fastener to a bone;
    a headpiece having a neck portion defining a bore which defines an inner wall having a second mating surface and a connector for retaining the longitudinal member;
    said first and second mating surfaces of said walls include means for sliding engagement of said fastener and said headpiece upon insertion of said upper portion into said bore while preventing relative rotation between said fastener and said headpiece; and
    a locking element which mechanically affixes said headpiece and said fastener together when said upper portion is disposed entirely within said bore.

2. The system of claim 1 wherein said upper portion of said fastener is frusto-conical in shape and wherein said second mating surface of said headpiece is adapted to correspondingly mate with said frusto-conical shape of said upper portion.

3. The system of claim 1 wherein said fastener includes a shoulder located between said upper and lower portions of said fastener for limiting the depth that said upper portion of said fastener can be inserted into said bore.

4. The system of claim 1 wherein said fastener contains a through bore thereby allowing said fastener to be cannulated.

5. The system of claim 1 wherein said headpiece includes an aperture adapted to receive a screw and said upper portion of said fastener defines a threaded internal bore for engaging said screw whereby said headpiece and said fastener are secured together.

6. The modular bone screw system of claim 1 wherein:
    said headpiece defines a centerline through said bore and includes a projection extending outwardly from said neck portion at an angle relative to said centerline, said projection terminating in said connector.

7. The system of claim 6 wherein said upper portion of said fastener is frusto-conical in shape and wherein said second mating surface of said headpiece is shaped to correspondingly mate with said frusto-conical shape of said upper portion.

8. The system of claim 7 wherein said upper portion of said fastener includes a fluted outer surface and said second mating surface of said headpiece is a fluted surface to correspondingly mate with said fluted outer surface of said upper portion of said fastener.

9. The system of claim 6 wherein said projection is angulated with respect to said centerline at an angle in the range of about 5° to 45°.

10. The system of claim 6 wherein said fastener contains a through bore thereby allowing said fastener to be cannulated and a shoulder which is located between said upper and lower portions of said fastener for limiting the depth that said upper portion of said fastener can be inserted into said bore.

11. The system of claim 6 wherein said headpiece includes an aperture adapted to receive a screw and said upper portion of said fastener defines a threaded internal bore for engaging said screw whereby said headpiece and said fastener are secured together.

12. The modular bone screw system of claim 1 wherein:
    said headpiece defines a centerline through said bore and includes a lateral section extending outwardly from said neck portion at an angle perpendicular to said center line, said lateral section terminating in said connector.

13. The system of claim 12 wherein said upper portion of said fastener is frusto-conical in shape and wherein said second mating surface of said headpiece is shaped to correspondingly mate with said frusto-conical shape of said upper portion.

14. The system of claim 12 wherein the length of said lateral section is in the range of about 5 millimeters to 3 centimeters.

15. The system of claim 12 wherein said fastener contains a through bore thereby allowing said fastener to be cannulated.

16. The system of claim 12 wherein said headpiece includes an aperture adapted to receive a screw and said upper portion of said fastener defines a threaded internal bore for engaging said screw whereby said headpiece and said fastener are secured together.

17. The system of claim 12 wherein said upper portion of said fastener includes a fluted outer surface and said second mating surface of said headpiece is a fluted surface to correspondingly mate with said fluted outer surface of said upper portion of said fastener.

18. The modular bone screw of claim 1 wherein:
said headpiece defines a centerline through said bore and a horizontal axis perpendicular to said centerline and includes
a lateral projection extending outwardly from said neck and terminating in said connector, said lateral projection being angulated relative to said horizontal axis.

19. The system of claim 18 wherein said projection is angulated with respect to a horizontal line defined by said neck at an angle in the range of 2° to 45° and the length of said lateral section is in the range of about 5 millimeters to 3 centimeters.

20. The system of claim 18 wherein said upper portion of said fastener is frusto-conical in shape and said second mating surface of said headpiece is shaped to correspondingly mate with said frusto-conical shape of said upper portion.

21. The system of claim 20 wherein said upper portion of said fastener includes a fluted outer surface and said second mating surface of said headpiece is a fluted surface to correspondingly mate with said fluted outer surface of said upper portion of said fastener.

22. The system of claim 18 wherein said fastener includes a shoulder located between said upper and lower portions of said fastener for limiting the depth that said upper portion of said fastener can be inserted into said bore.

23. The system of claim 18 wherein said headpiece includes an aperture adapted to receive a screw and said upper portion of said fastener defines a threaded internal bore for engaging said screw whereby said headpiece and said fastener are secured together.

24. The system of claim 1 in which the longitudinal member has an opening defined therethrough, and wherein said connector includes an elongated shank configured to extend through the opening in the longitudinal member.

25. The system of claim 1 wherein said upper portion of said fastener includes a fluted outer surface and said second mating surface of said headpiece is a fluted surface to correspondingly mate with said fluted outer surface of said upper portion of said fastener.

26. The system of claim 1 wherein said connector defines an aperture sized to receive the longitudinal member therethrough.

27. An apparatus for connecting a longitudinal member to a bone, comprising:
a bone engaging fastener having an upper portion defining a threaded internal bore and a lower portion configured for engaging the bone;
a headpiece defining a bore for receiving said upper portion of said fastener therein and including a connector configured for retaining the longitudinal member;
means between said upper portion of said fastener and said bore of said headpiece for preventing relative rotation therebetween; and
a locking element extendable into said bore and having a threaded portion for threaded engagement with said threaded internal bore of said fastener, and an enlarged head for bearing against said headpiece as said threaded portion is threaded into said internal bore.

28. The apparatus according to claim 27, wherein said upper portion of said fastener and said bore of said headpiece define mating surfaces configured for sliding engagement between said upper portion and said bore along an axis of said bore.

29. The apparatus according to claim 28, wherein said mating surfaces are fluted surfaces.

30. The apparatus according to claim 28, wherein said mating surfaces are frusto-conical surfaces.

31. The apparatus according to claim 30, wherein said frusto-conical surfaces define increasing mating diameters that are larger adjacent said lower portion of said bone engaging fastener.

32. The apparatus according to claim 27, wherein:
said headpiece includes an aperture communicating with said bore, said aperture sized to prevent insertion of said upper portion therethrough; and
said locking element is sized to extend through said aperture for engagement with said upper portion of said fastener.

33. The apparatus according to claim 22, wherein said bone engaging fastener includes a shoulder located between said upper and lower portions thereof, said shoulder sized to prevent insertion of said fastener.

34. The apparatus according to claim 27 in which the longitudinal member is an elongated rod, wherein said connector defines an aperture sized to receive the elongated rod therethrough.

35. The apparatus according to claim 34, wherein:
said connector defines a threaded opening intersecting said aperture; and
said connector includes a set screw for threaded engagement within said threaded opening to bear against the elongated rod disposed within said aperture.

36. The apparatus according to claim 27, in which the longitudinal member is an elongated plate having an opening defined therethrough, wherein said connector includes an elongated shank configured to extend through the opening in the elongated plate.

37. The apparatus according to claim 36, wherein said elongated shank is threaded and said connector includes an internally threaded nut for engaging said shank to clamp the elongated plate to said connector.

38. The apparatus according to claim 36, wherein said bore of said headpiece defines a centerline therethrough and said elongated shank defines a longitudinal axis along its length that is substantially parallel to said centerline.

39. The apparatus according to claim 36, wherein said bore of said headpiece defines a centerline therethrough and said elongated shank defines a longitudinal axis along its length that intersects said centerline.

40. The apparatus according to claim 36, wherein said bore of said headpiece defines a centerline therethrough and said elongated shank defines a longitudinal axis along its length that is angulated with respect to said centerline.

41. The apparatus according to claim 40, wherein said longitudinal axis is angulated relative to said centerline at an angle of between about 5° and 45°.

42. The apparatus according to claim 27, wherein said headpiece includes an elongated section between said bore and said connector.

43. The apparatus according to claim 42, wherein said bore defines a centerline therethrough and said elongated section defines an axis along its length that is substantially perpendicular to said centerline.

44. The apparatus according to claim 42, wherein said bore defines a centerline therethrough, said headpiece defines a horizontal axis that is perpendicular to said centerline, and said elongated section defines an axis along its length that is angulated relative to said horizontal axis.

45. The apparatus according to claim 44, wherein said axis of said elongated section is angulated above said horizontal axis in relation to said bone engaging fastener when said upper portion of said fastener is disposed within said bore.

46. The apparatus according to claim 44, wherein said axis of said elongated section is angulated below said horizontal axis in relation to said bone engaging fastener when said upper portion of said fastener is disposed within said bore.

47. The apparatus according to claim 44, wherein said axis of said elongated section is angulated at an angle of between about 2° and 45°.

48. The apparatus according to claim 42, wherein said elongated section has a length of between about 0.5 cm. and 3.0 cm.

49. The apparatus according to claim 27, wherein said lower portion of said fastener includes bone engaging threads.

* * * * *